United States Patent
Zhou et al.

(10) Patent No.: US 6,706,066 B1
(45) Date of Patent: Mar. 16, 2004

(54) FLOATING PHAKIC REFRACTIVE LENS DESIGN FOR PRESERVING EYE DYNAMICS

(75) Inventors: Stephen Q. Zhou, Irvine, CA (US); Christopher D. Wilcox, Mission Viejo, CA (US)

(73) Assignee: Medennium, Inc., Irvine, CA (US)

( * ) Notice: Subject to any disclaimer, the term of this patent is extended or adjusted under 35 U.S.C. 154(b) by 98 days.

(21) Appl. No.: 09/597,345

(22) Filed: Jun. 19, 2000

Related U.S. Application Data

(60) Provisional application No. 60/152,052, filed on Sep. 2, 1999.

(51) Int. Cl.[7] .................................................. A61F 2/16
(52) U.S. Cl. ....................................................... 623/6.56
(58) Field of Search ............................... 623/6.11–6.62

(56) References Cited

U.S. PATENT DOCUMENTS

| | | | | |
|---|---|---|---|---|
| 4,254,511 A | * | 3/1981 | Chase et al. | 623/6.11 |
| 4,424,597 A | * | 1/1984 | Schlegel | 623/6.11 |
| 4,585,456 A | | 4/1986 | Blackmore | 623/6 |
| 4,702,244 A | * | 10/1987 | Mazzocco | 623/6.25 |
| 5,258,025 A | | 11/1993 | Fedorov et al. | 623/6 |
| 5,480,428 A | | 1/1996 | Fedorov et al. | 623/6 |
| 6,066,172 A | * | 5/2000 | Huo et al. | 623/6.56 |
| 6,152,958 A | * | 11/2000 | Nordan | 623/6.25 |

FOREIGN PATENT DOCUMENTS

| | | |
|---|---|---|
| WO | 9817205 | 10/1997 |

* cited by examiner

*Primary Examiner*—David H. Willse
*Assistant Examiner*—Javier G. Blanco
(74) *Attorney, Agent, or Firm*—Frost Brown Todd LLC

(57) ABSTRACT

Phakic refractive lens (PRL) for correcting myopia or hyperopia are disclosed. The lens is implanted in the posterior chamber of the eye, with no permanent point of fixation, such that it floats between the patient's iris and natural lens. The lens corrects refractive errors in the eye, while maintaining the fluid dynamics of the eye and not causing stress or damage to eye structures. The lenses are made from a flexible material (such as those having a hardness of from about 20 to about 50 Shore A), having a specific gravity of from about 0.9 to about 1.2 $g/cm^3$, and have a mass per unit area of from about 0.03 to about 0.30 $mg/mm^2$. The method for using those lenses and surgical kits including those lenses are also disclosed.

18 Claims, 4 Drawing Sheets

FLOATING PHAKIC REFRACTIVE LENS DESIGN FOR PRESERVING EYE DYNAMICS

PROBLEM TO BE SOLVED

This application is based on U.S. provisional application No. 60/152,052, Zhou and Wilcox, filed Sep. 2, 1999.

A posterior chamber phakic refractive lens (PRL) is surgically implanted behind the iris and in front of the human natural crystalline lens for correcting myopia or hyperopia. The PRL is the only reversible procedure for correcting severe refractive errors in both myopic and hyperopic patients. However, there are three major complications associated with the PRL implantation. They are: (1) intraocular pressure (IOP) elevation; (2) cataract induction; and (3) iris pigment dispersion. Only when all of these three complications are successfully resolved will PRL technology become acceptable to surgeons and patients. Currently, IOP elevation has been successfully controlled by surgical iridotomy (i.e., two holes made in the iris either by laser or knife). Cataract induction and iris pigment dispersion remain as the major complications for PRL implantation.

The present invention aims to define a number of requirements, including PRL material characteristics, for a floating PRL design which preserves eye dynamics. Such a floating PRL design solves the problems of cataract induction and iris pigment dispersion caused by the implantation of a PRL.

PRIOR ART

There are a number of patents describing the posterior chamber PRL concept and specific lens designs. U.S. Pat. No. 4,585,456, Blackmore, issued Apr. 29, 1986, discloses a phakic intraocular lens (IOL) composed of flexible materials which is positioned against the natural lens of the eye and is held in place immediately adjacent to.the natural lens and the ciliary sulcus. There are no specific disclosures of the PRL material properties, such as softness. The lens does not float in the eye but, rather, is fastened in place.

Other patents describe different ways of reducing IOP elevation and avoiding cataract formation by PRL designs and their fixation mechanisms. For example, Fedorov, in U.S. Pat. No. 5,480,428, issued Jan. 2, 1996, discloses a novel phakic lens design which has an opening through the center of the optic body. This open hole allows aqueous humor to flow through the lens body, thereby preventing IOP elevation, but it reduces the optical performance of the phakic lens. This patent also does not disclose the lens material properties or lens surface properties for such lens designs. Fedorov, in U.S. Pat. No. 5,258,025, issued Nov. 2, 1993, discloses that post-operative inflammation, caused by the contacting of the supporting elements with the ocular tissue, is prevented by moving supporting elements to the periphery of the phakic lens. The Zinn's zonules are strong enough to hold the supporting elements in place without causing inflammation. Again, Fedorov failed to specify the lens material properties and lens surface properties. Further, this is not a floating lens design.

Finally, PCT Published Application WO 98/17205, Valunin et al., published Apr. 30, 1998, describes the structure of a phakic IOL, which floats in the eye. Valunin taught that the phakic IOL can be made from, for example, silicone, silicone-methacrylate copolymers, poly(methyl methacrylate), poly(hydroxyethyl methacrylate) and collagen/acrylate blends. However, no specific properties of a suitable material, such as mass per unit area or specific gravity, are defined.

Accordingly, there is a great need to identify desirable lens materials with required properties which, in combination with proper lens specifications, can preserve the eye dynamics after PRL implantation. The combination of lens design and the lens material properties makes it possible to avoid cataract induction and iris pigment dispersion. Neither the lens design alone nor the lens material properties alone can achieve the desirable floating features.

SUMMARY OF THE INVENTION

The object of the current invention is to provide a PRL, with a proper lens design and material properties, that may be placed in the posterior chamber of the human eye for correction of refractive errors. It is also the object of this invention to provide a PRL that can float in aqueous humor and that is very flexible and soft. The floating action and soft nature of the PRL will preserve the eye dynamics so that cataract induction of the human crystalline lens will be avoided and iris pigment dispersion eliminated. It is further an object of the present invention that this floating design and these benefits be achieved by selecting biocompatible materials having defined properties and by selecting other parameters, such as low mass per unit surface area (grams/$mm^2$), of the PRL. It is a still further object of this invention that, due to the softness of the PRL material and the floating nature of the PRL design, when the iris contracts, it can move freely and constantly over the anterior surface of the PRL without causing iris pigment dispersion.

These and other objects are accomplished by a phakic refractive lens for implantation in the posterior chamber of the eye, said lens having no permanent fixation in the posterior chamber other than simple floating in the aqueous humor when positioned between the iris and the natural crystalline lens, said lens having the following properties:

(a) mass per unit surface area of from about 0.03 to about 0.30 $mg/mm^2$, preferably from about 0.05 to about 0.13 $mg/mm^2$;

(b) specific gravity of the materials used for said lens of from about 0.9 to about 1.2 $grams/cm^3$; and (c) the lens must be flexible, preferably the hardness of the material used for said lens being from about 20 to about 50 Shore A.

The present invention also encompasses a method for correcting the vision of a myopic or hyperopic patient comprising implanting a phakic refractive lens in the eye of said patient, said lens floating in the aqueous humor between the patient's iris and natural lens with no permanent point of fixation, said phakic refractive lens having the following properties:

(a) the mass per unit area of the lens if from about 0.03 to about 0.30 $mg/mm^2$;

(b) the lens is flexible; and (c) the specific gravity of the materials comprising the lens is from about 0.9 to about 1.2 $g/cm^3$.

DETAILED DESCRIPTION OF THE INVENTION

There are many factors affecting the formation of cataracts after implantation of a PRL. First, if a PRL directly contacts the natural crystalline lens, it causes stress on that lens. As a result, a subcapsular cataract may develop. Second, disturbance of eye dynamics can also induce cataract formation. Since the PRL is positioned between the iris and the human natural crystalline lens, it nearly blocks the whole pupil. Although an iridotomy is typically performed to successfully prevent IOP elevation, the blockage of the pupil by the PRL still inhibits the free exchange of aqueous humor between the anterior chamber and posterior chamber of the eye, thereby disturbing the eye dynamics. This may result in accelerated formation of cataracts. A floating PRL design will maximize the exchange of aqueous humor between the posterior chamber and anterior chamber, preserving the eye dynamics. As a result, it avoids cataract induction. Finally, the PRL of the present invention is so flexible and soft that it yields to the iris when a contact occurs. The iris feels the PRL as if it were part of the aqueous humor, avoiding iris pigment dispersion.

Figure 1:
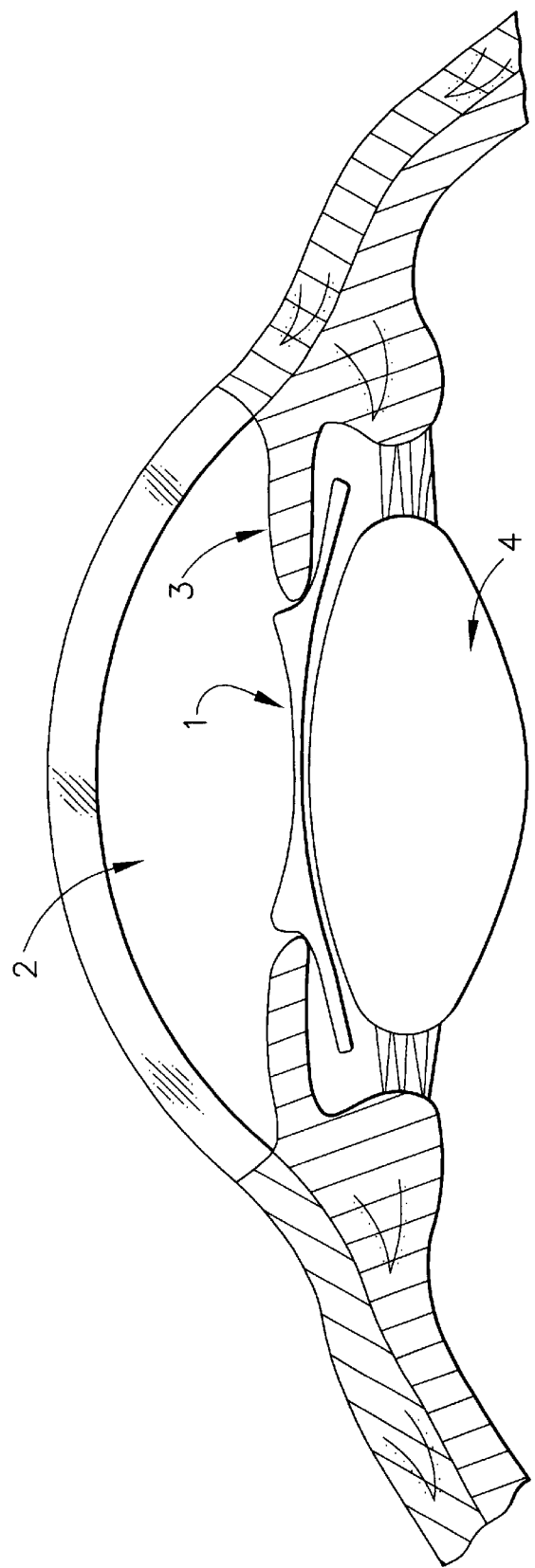
FIG. 1 is a cut-away view of the eye showing the positioning of the lens of the present invention.

The primary feature of the floating PRL design of the present invention is that it does not have any permanent fixation mechanism. The PRL (1) simply floats in the aqueous humor (2) as shown in FIG. 1. In that figure, the PRL is positioned between the iris (3) and the natural lens (4) in the eye. The lens has a structure of the type shown in PCT Published Application 98/17205, Valunin, et al., published Apr. 30, 1998, and U.S. Pat. No. 6,015,435, Valunin, et al., issued Jan. 18, 2000, both incorporated herein by reference. Therefore, it does not cause any permanent stress against the human crystalline lens. Due to its floating nature, the PRL is constantly changing its location within the boundary determined by the haptics. When the iris (3) contracts and moves toward the center of the anterior surface of the PRL, the iris may exert some pressure via the PRL to the natural crystalline lens (4). Because of its floating nature, the PRL does not have any localized pressure points against the human crystalline lens. This floating PRL simply transmits the pressure in any direction as if it were part of the aqueous medium. This way, the stress on the natural crystalline lens caused by iris movement is dissipated by the floating PRL much the same way as by the aqueous humor. As a result, cataract induction by the PRL implantation is minimized.

The second feature of the floating PRL design is that it allows the iris to move freely and constantly on its anterior surface without causing iris pigment dispersion. When the iris contracts or dilates, the PRL yields to the iris movement because of the floating feature and the softness of the PRL material. The iris "feels" the PRL as if the PRL were part of the aqueous humor so that iris pigment dispersion is avoided.

The third feature of the floating PRL design is that it allows the aqueous humor to flow from posterior chamber to anterior chamber. In healthy eyes, this outflow occurs constantly. An ideal PRL should have a large surface area and a small mass. The materials used for making PRLs should be very soft and flexible. All of these properties are critical factors for the formulation of a floating PRL to allow the maximum outflow of the aqueous humor.

Figure 3:
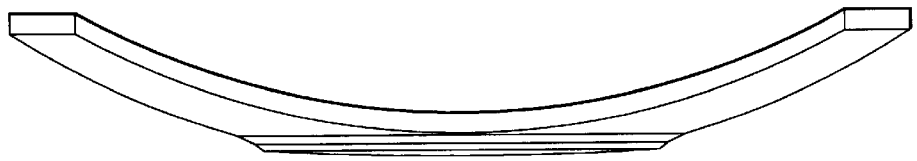
FIG. 3 is a side view of a lens of the present invention (see Examples 1 and 2).
Figure 5:
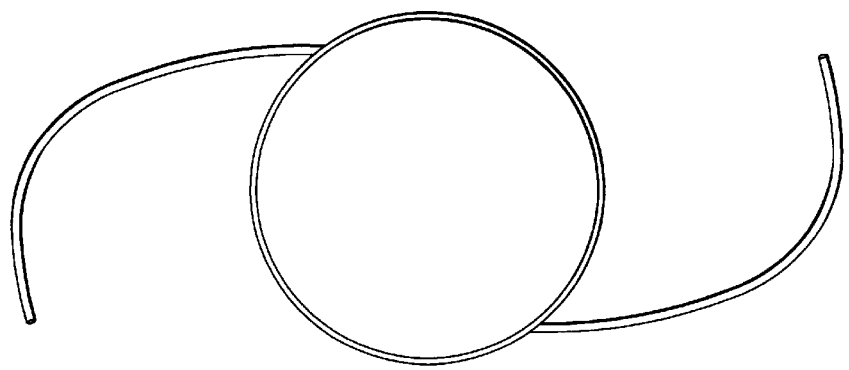
FIG. 5 is a top view of a prior art fixed position intraocular lens (see Example 3).
Figure 4:
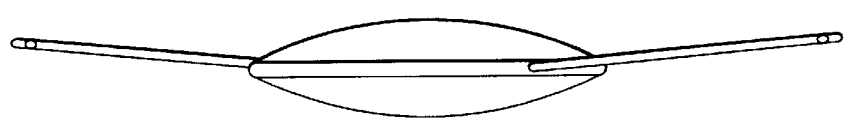
FIG. 4 is a side view of a prior art fixed position intraocular lens (see Example 3).

Those who are skilled in the art understand that the specific gravity of the aqueous humor of the human eye is approximately equal to that of water (1 gram/cm$^3$) and that any article which can float in water has to have a weight equal to or slightly lighter than 1 gram/cm$^3$. However, some materials with a much larger specific gravity (such as 1.2 g/cm$^3$, as shown in Example 5) than that of the aqueous humor can still be used to achieve a floating design. The following example clearly illustrates how a material which is heavier than water can be used to make a PRL that floats in water. It was surprisingly-found that PRLs made from a medical grade silicone with a specific gravity of 1.05 float on the water surface while a cataract intraocular lens (IOL) made from the same medical grade silicone does not float on the water surface (see Examples 2 and 3). The silicone PRL can be forced into water. However, as soon as the force is released, the silicone PRL floats back to the water surface. On the other hand, the prior art cataract IOL made from the same silicone material can only float on the water surface when it is very cautiously placed on that water surface. When the water is slightly disturbed or the cataract IOL is forced into the water, it does not float back on the water surface again. The only difference in this set of experiments is the shape of the PRL (FIGS. 2 and 3) and the cataract IOL (FIGS. 4 and 5).

Figure 2:
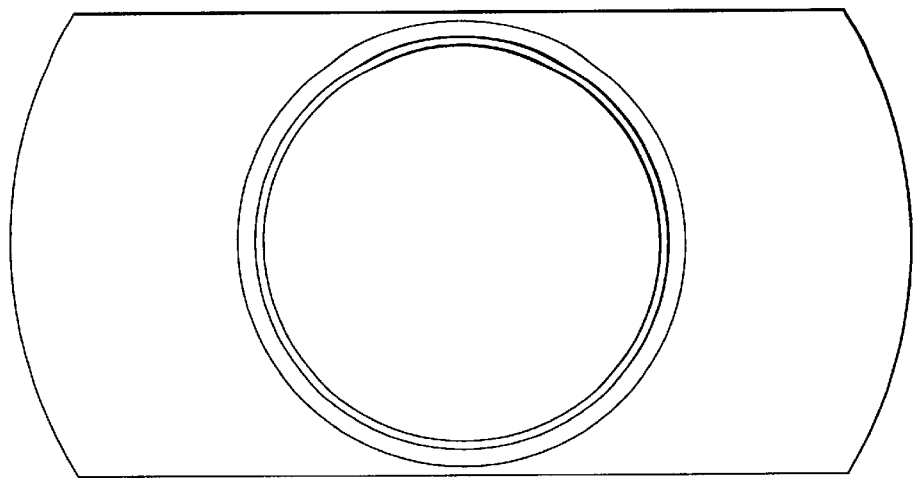
FIG. 2 is a top view of a lens of the present invention (see Examples 1 and 2).

As shown in FIG. 2, the PRL has a relatively large surface area. The linear dimensions are approximately 6×11 mm. This is equivalent to a surface area of about 132 mm$^2$. Typically, PRLs with configurations as shown in FIGS. 2 and 3 weigh about 15 mg or less. Therefore, the mass per unit surface area for the PRL is approximately 0.11 mg/mm$^2$. On the other hand, a cataract IOL (see FIGS. 4 and 5) typically has an optical diameter of 6 mm and weighs about 20 mg. Therefore, the mass per unit surface area for the cataract IOL is approximately 0.31 mg/mm$^2$. The silicone used in this case is a typical hydrophobic material with a contact angle of 95°. The hydrophobicity of the PRL creates a considerable surface tension between the PRL and water. This surface tension is the driving force for keeping the PRL floating. There exists a balance between the two opposite forces: gravity and surface tension. Preferred hydrophobic materials for use in the present invention have a contact angle of about 80° or higher, most preferably about 90° or higher. PRLs made from materials with a specific gravity greater than about 1.0 have a tendency to not float on water. However, the surface tension between a hydrophobic PRL and water keeps the PRL floating on water surface even if its specific gravity is greater than about 1.0. Increasing the specific gravity will decrease the floatability while increasing the surface area or reducing the mass of the PRL or both will increase the floatability. Given a material, the determining factor for a floating PRL is the ratio of mass per unit surface area. As shown in above example, the mass per unit surface area for the PRL of the present invention is approximately 0.11 mg/mm$^2$ and for the prior art cataract IOL is approximately 0.31 mg/mm$^2$. It is therefore concluded that if a PRL's mass per unit surface area is equal to or greater than about 0.31 mg/mm$^2$, it may not be used effectively for a floating lens design. Thus, the mass per unit surface area of the lens of the present invention should be from about 0.03 to about 0.30, preferably from about 0.05 to about 0.30, most preferably from about 0.05 to about 0.13 mg/mm$^2$.

The comparison of the silicone PRL and the silicone cataract IOL given in above discussion (i.e., Examples 2 and 3), is only for the purpose of illustration. It clearly demonstrates that the mass per unit surface area, not the specific gravity, is the determining factor for a floating PRL design. This principle applies to PRLs made from hydrophilic material as well. It is important to mention that it is not necessary for a PRL to float on the water surface to obtain the benefits of the present invention. In fact, it is more desirable to have a PRL which can float in water instead of on the water surface. This is because the inside of the eye is filled with aqueous humor and the PRL is suspended in the aqueous humor. To simulate the PRL implanted in the eye, a PRL which can float in water temporarily when water is disturbed slightly, will have met the design feature. This is because, in healthy eyes, aqueous humor always flows from posterior chamber to anterior chamber. When such an outflow occurs, it is very important that the PRL floats to allow the aqueous humor to pass by, therefore preserving the eye dynamics. Furthermore, the outflow of the aqueous humor avoids direct contact of the PRL with the natural crystalline lens and thereby avoids cataract induction by the implantation of a PRL.

It was found that PRLs made from hydrophilic materials, such as poly(hydroxyethyl methacrylate) (polyHEMA), the classic example of a hydrogel material, can temporarily float in water when the mass per surface area criteria are met. When fully hydrated in water, polyHEMA hydrogel has a contact angle of 34°. Preferred hydrophilic materials have a contact angle of about 40° or less.

This unexpected discovery is very important for a number of reasons. First, most polymeric materials have a specific gravity greater than about 1. This invention allows the use of such materials for a floating PRL design. Second, the current invention will lead engineers to design a PRL with a maximum surface area and a minimum weight in order to maximize the floating design features. Finally, the relationship of various factors needs to be considered in order to maximize the floating feature. For example, when a material with high specific gravity is used for the floating PRL design, its surface area can be increased or its total weight can be decreased or both in order to compensate the negative effect by the increase in the specific gravity.

In summary, the most critical factor for a floating PRL design is not the specific gravity but the mass per unit surface area (milligram/mm$^2$). Experiments indicate materials with specific gravity greater than about 1.0 g/cm$^3$ can be used for the floating design if its mass/area is minimized. For example, an acrylic material with a specific gravity of 1.2 gram/cm$^3$ can be used to achieve the floating features (Example 5). In general, the materials useful in the present invention will have a specific gravity of from about 0.9 to about 1.2, preferably from about 1.0 to about 1.2 g/cm$^3$, and most preferably from greater than about 1.0 to about 1.2 g/cm$^3$. Finally, the materials used for making the lenses of the present invention should be flexible, preferably having a hardness of from about 20 to about 50 Shore A. This will allow the lens to maintain its shape for proper functioning, but will also give it sufficient flexibility for insertion into the eye and for non-damaging interactions with the iris and the natural lens in the eye. In some instances it may be possible to use materials having a hardness greater than 50 Shore A, if that material (for example, poly(methyl methacrylate)) can be made flexible by using it at very small thicknesses (see Examples 7 and 8), or (for example, poly (hydroxyethyl methacrylate)) by hydrating it (see Example 6).

A logical extension of the present invention is that if the surface area of the PRL is increased, such as by roughening the surface of the non-optical portion of the lens, the value of the mass per unit surface area of the lens is decreased, thereby forming a more effective floating PRL, even for lenses with somewhat higher masses.

Preferred materials for use in formulating the lenses of the present invention include silicones, poly(acrylates), poly (methacrylates), hydrogels, collagen-containing polymers, and mixtures of those materials.

The present invention also encompasses a kit which comprises the phakic refractive lens described above together with a means for inserting the lens into the posterior chamber of the eye such that it floats in the aqueous humor of the eye between the patient's iris and natural lens, without any point of permanent fixation. Such means may include one or more of the following: an instrument for making the required incision in the cornea, an instrument for inserting the phakic lens into the eye, an instrument for correctly placing the phakic lens in the eye, means for closing the corneal incision, and instructions for the implanting of the lens in the eye.

EXAMPLES

The following examples are given for the purpose of illustrating the present invention and are not intended to be limiting thereof.

Contact angle is a measurement of surface hydrophobicity (or hydrophilicity). In the present invention, Sessile Drop method and a Rame-Hart,Goniometer are used for the measurement. In a typical test, the average of 12 readings is used for reporting purposes. A typical hydrophobic material, such as silicone, usually has a contact angle in the range of about 80° or higher, while a typical hydrophilic material, such as poly-HEMA, has a contact angle in the range of about 40° or lower.

Example 1

Floating Silicone PRL

SIEL 1.46 is a silicone material with a refractive index of 1.46 and specific gravity of 1 (commercially available from SIEL, Ltd. a specialty silicone supplier in Russia). A small amount of the material (Part A: Part B=10:1 by weight) (about 30 mg or less) is placed onto a PRL metal mold. The mold is clamped and placed in a pre-heated oven at 120° C. for 70 minutes. The mold is then cooled down to about room temperature. The mold is opened and the PRL carefully removed from the mold. The PRL has a configuration and dimensions as shown in FIG. 2.

The PRL is placed in deionized water and observed to float on the water surface. A spatula or forceps can be used to gently push the PRL into the water. However, as soon as the pushing force is released, the PRL will float back onto the water surface. Even when the whole PRL is pulled into the water, it comes back on the water surface as soon as the pulling-force is released. The contact angle of the PRL is 80°. The Shore A hardness of the PRL material is in the range of 20 to 25.

The PRLs with configurations shown in FIGS. 2 and 3 typically weigh 15 milligrams or less. The surface area of the PRL is approximately 132 mm$^2$. Therefore, the mass per unit surface area is approximately 0.11 milligrams/mm$^2$ or less.

Example 2

Floating Silicone PRL

A silicone material Med 6820, manufactured by NuSil Silicone Technology, is used to prepare PRLs under the following conditions. Equal amounts of Part A and Part B are mixed for 10 minutes. The mixture is transferred to a syringe and degassed under vacuum until all the visible air bubbles disappear. A very small amount of the mixture is poured into a metal alloy mold and cured at 120° C. for 70 minutes. The PRL is removed from the mold and placed in DI water with its posterior side facing down. The PRL is observed to float on the water surface. When a spatula or forceps is used to gently push the PRL into the water, the PRL floats back onto the water surface as soon as the spatula is removed from the PRL.

Other physical and mechanical properties of the Med 6820 silicone material are as follows: tensile strength=750 psi; elongation=125%; refractive index=1.43; specific gravity=1.05 g/cm$^3$ at room temperature. The specific gravity measurement is based on ASTM D792 Specific Gravity and Density of Plastics by Displacement, using a Cahn DCA312 Dynamic Contact Angle Analyzer. The contact angle, as measured by Sessile Drop Method, using a Rame-Hart Goniometer is 95°. The hardness is in the range of 40 to 50 Shore A.

The shape and dimensions of the PRL are the same as that in Example 1. The mass per unit surface area in this case is approximately 0.12 milligrams/mm$^2$.

Example 3 (Comparative)

Non-floating Silicone Cataract Intraocular Lens (IOL)

By way of comparison, a non-floating lens is made as follows. Using the identical silicone material as in Example 2, i.e., Med 6820 by NuSil Silicone Technology, a regular intraocular lens (IOL) for cataract surgery is molded, instead of a PRL. This cataract IOL has a shape and dimensions illustrated in FIGS. 4 and 5.

The cataract IOL is placed in DI water and it is observed that the cataract IOL does not float on the water surface or in the water, and it sinks to the bottom of the container. It requires a much larger force to disturb water in order to let the IOL temporarily float in water. This is because the mass of this cataract lens is much larger than that of the floating force. In this case, the surface area of the cataract IOL is approximately 64 mm$^2$. The cataract IOL weighs 20 mg. Therefore, the mass per unit surface area for this cataract IOL is approximately 0.31 mg/mm$^2$, more than twice as large as that of the lenses of the present invention illustrated in Examples 1 and 2.

Example 4

Floating Acrylic PRL

A mixture of 15.2 grams of hexylmethacrylate, 4.8 grams of methylmethacrylate, 0.07 gram of ethylene glycol dimethacrylate, and 0.02 gram of benzoyl peroxide is purged with argon and then heated at 100° C. to prepare a viscous syrup. The syrup is still flowable when it is swirled. The syrup is then transferred to a glass lens mold and placed in an oven at 100° C. overnight (approximately 16 hours). The mold is cooled down to room temperature and opened to obtain a positive powered lens.

The configuration of the lens is illustrated in FIG. 4. Its overall diameter is about 10.5 mm and optical diameter is about 5 mm. When the lens is placed in deionized water with the posterior side facing down, it floats on the water surface. The PRL can be forced into the water. However, the PRL can float in water when it is slightly disturbed. The specific gravity of lens material is measured to be 1.09 g/cm$^3$. The contact angle of this copolymer of hexylmethacrylate and methacrylate is measured to be 76°. The lens weighs 21 mg and its surface area is approximately 174 mm$^2$. Therefore, the mass per unit surface area in this case is about 0.12 mg/mm$^2$.

Other properties of this acrylic material are as follows: refractive index: 1.482; glass transition temperature=23° C.; hardness=47 Shore A.

Example 5

Floating Acrylic PRL

Figure 7:
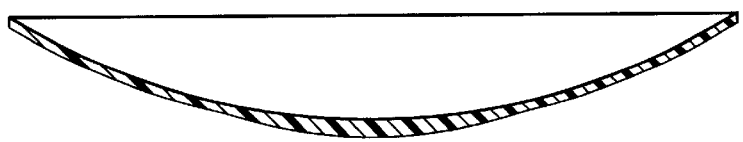
FIG. 7 is a side view of a lens of the present invention (see Example 4).
Figure 6:
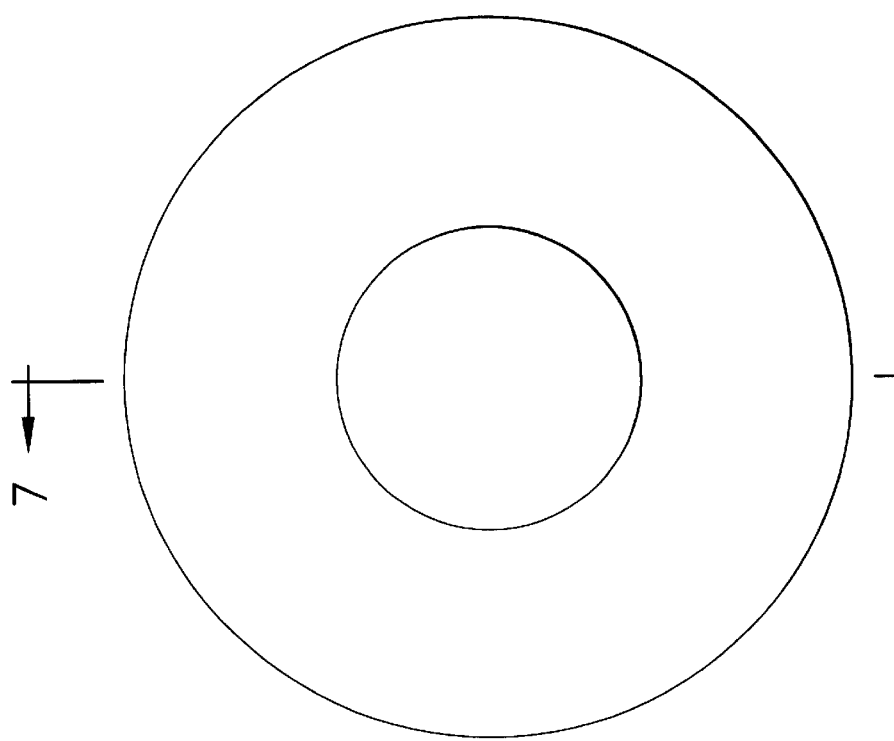
FIG. 6 is a top view of a lens of the present invention (see Example 4).

A mixture of 48 grams of ethylene glycol phenyl ether acrylate, 2 grams of bisphenol A propoxylate diacrylate, 0.65 grams of 2-(4-benzoyl-3-hydroxyphenoxy) ethyl acrylate, and 50 milligrams of azobisisobutyronitrile is de-aired with ultra-pure nitrogen gas for about 15 minutes. This mixture can be used for making the PRL directly or can be pre-gelled. In either case, the mixture is transferred into a mold. Curing conditions are: temperature 90–110° C.; time=11–16 hours. Other properties of this acrylic material are: refractive index=1.558; glass transition temperature=7° C.; Shore A hardness 36; tensile strength %=280; elongation %=160%. The specific gravity of this material is 1.2 grams/cm$^3$. The contact angle of this polymer is 81°. The PRL weighs 23.2 milligrams. The PRL shape and dimensions are same as that in Example 4 (FIGS. 6 and 7). The surface area is approximately 173 mm$^2$. Therefore, the mass per unit surface area for this PRL is approximately 0.13 mg/mm$^2$.

When this PRL is placed in deionized water with the posterior side facing down, it floats on the water surface. The PRL can be forced into the water. However, the PRL can float in water when it is slightly disturbed.

Example 6

Floating Hydrophilic Lens

A procedure similar to that of Example 4 is followed except a different composition is used. The new composition comprises a mixture of 5 grams of 2-hydroxyethyl methacrylate (HEMA), 0.25 gram of ethylene glycol dimethacrylate, and 5 mg of benzoyl peroxide. The lens made from this composition does not float on the water surface. However, it can float for a few seconds in water when the water solution is slightly stirred. Such a temporary floating can also meet the requirement of a floating PRL design. Inside the eye the aqueous humor flows from posterior chamber to anterior chamber. When such an aqueous humor flow occurs, a floating PRL will yield to the aqueous outflow, thereby preserving eye dynamics.

The non-hydrated poly(hydroxyethyl methacrylate) has a specific gravity of 1.15 g/cm$^3$. It is a solid, hard material and its hardness exceeds the Shore A scale. The mass per unit surface area for the dry poly(hydroxyethyl methacrylate) lens is about 0.12 mg/mm$^2$. However, when it is hydrated, poly(hydroxyethyl methacrylate) absorbs about 40% water and becomes soft. The contact angle of the fully hydrated lens is 34°.

Example 7

A very thin disc is cut by lathe out of poly(methyl methacrylate) (PMMA) material. PMMA has specific gravity of 1.19 g/cm$^3$ and is a hard solid polymer with a Rockwell hardness of M-93. Its hardness exceeds the Shore A hardness scale and, therefore, it cannot be measured by Shore A method. The disc has a radius of 6 mm and a thickness of about 0.07 mm. It weighs about 9 mg. Therefore, the mass per surface area is about 0.04 mg/mm$^2$. The disc was found to be able to float on a water surface. Without external force applied to the disc, it always floats on the water surface. However, it can be forced into water. When water is slightly disturbed, the disc can float in water. Furthermore, although PMMA material is a hard solid, when it is machined into a disc with a thickness of about 0.07 mm, it becomes much more flexible, For example, it can be rolled up without breaking the disc.

Example 8

A similar disc was also cut out of PMMA material with a radius of about 5 mm and thickness of 0.28 mm. The disc weighs about 26 mg. Therefore, the mass per surface area is 0.17 mg/mm$^2$. The disc is found to be able to float on a water surface. Without external force applied to the disc, it always floats on the water surface. However, the disc can be forced into water. When water is slightly disturbed the disc can also float in water.

We claim:

1. A phakic refractive lens, said lens structurally adapted for implantation in the posterior chamber of the eye so as to float in the aqueous humor between the iris and the natural lens, said lens having met the following properties:
   a) the mass per unit area of the lens is from about 0.03 to about 0.30 mg/mm$^2$;
   b) the lens is flexible; and
   c) the specific gravity of the materials comprising the lens is from about 0.9 to about 1.2 g/cm$^3$.

2. The phakic refractive lens according to claim 1 wherein the materials comprising the lens have a hardness of from about 20 to about 50 Shore A.

3. The phakic refractive lens according to claim 2 having a mass per unit area of from about 0.05 to about 0.30 mg/mm$^2$.

4. The phakic refractive lens according to claim 3 wherein the specific gravity of the materials comprising the lens is from about 1.0 to about 1.2 g/cm$^3$.

5. The phakic refractive lens according to claim 4 having a mass per unit area of from about 0.05 to about 0.13 mg/mm$^2$.

6. The phakic refractive lens of claim 5 made from a hydrophobic material.

7. The phakic refractive lens of claim 5 made from a hydrophilic material.

8. The phakic refractive lens according to claim 5 made from a material selected from the group consisting of silicone, poly(acrylates), poly(methacrylates), hydrogels, collagen-containing polymers, and mixtures thereof.

9. The phakic refractive lens according to claim 1 which floats on or in DI water.

10. A method for correcting the vision of a myopic or hyperopic patient comprising implanting a phakic refractive lens in the eye of said patient, said lens floating in the aqueous humor between the patient's iris and natural lens with no permanent point of fixation, said phakic refractive lens having the following properties:
    a) the mass per unit area of the lens is from about 0.03 to about 0.30 mg/mm$^2$;
    b) the lens is flexible; and
    c) the specific gravity of the materials comprising the lens is from about 0.9 to about 1.2 g/cm$^3$.

11. The method according to claim 10 wherein the phakic refractive lens floats on or in DI water.

12. The method according to claim 10 wherein the materials comprising the phakic refractive lens have a hardness of from about 20 to about 50 Shore A.

13. The method according to claim 12 wherein the phakic refractive lens has a mass per unit area of from about 0.05 to about 0.30 mg/mm$^2$.

14. The method according to claim 13 wherein the specific gravity of the materials comprising the phakic refractive lens is from greater than about 1.0 to about 1.2 mg/cm$^3$.

15. The method according to claim 14 wherein the phakic refractive lens has a matter/per unit area of from about 0.05 to about 0.13 mg/cm$^2$.

16. The method according to claim 15 wherein the phakic refractive lens is made from a material selected from the group consisting of silicone, poly(acrylate), poly(methacrylate), hydrogels, collagen-containing polymers, and mixtures thereof.

17. A kit comprising:
    (1) a phakic refractive lens, said lens structurally adapted for implantation in the posterior chamber of the eye, said lens having the following properties:
        a) the mass per unit area of the lens is from about 0.03 to about 0.30 mg/mm$^2$;
        b) the lens is flexible; and
        c) the specific gravity of the materials comprising the lens is from about 0.9 to about 1.2 g/cm$^3$;
    (2) means for implanting said phakic refractive lens in the eye of a patient such that the lens is floating in the aqueous humor of the eye between the patient's iris and natural lens with no permanent point of fixation.

18. The kit according to claim 17 wherein the materials comprising the phakic refractive lens have a hardness of from about 20 to about 50 Shore A.

* * * * *